(12) United States Patent
Buechner et al.

(10) Patent No.: US 8,779,188 B2
(45) Date of Patent: Jul. 15, 2014

(54) PROCESS FOR THE PRODUCTION OF L-CARNITINE TARTRATE

(75) Inventors: Thomas Buechner, Naters (CH); Uwe Zacher, Brig (CH)

(73) Assignee: Lonza Ltd., Visp (CH)

( * ) Notice: Subject to any disclaimer, the term of this patent is extended or adjusted under 35 U.S.C. 154(b) by 237 days.

(21) Appl. No.: 13/225,863

(22) Filed: Sep. 6, 2011

(65) Prior Publication Data

US 2012/0059189 A1    Mar. 8, 2012

Related U.S. Application Data

(60) Provisional application No. 61/380,392, filed on Sep. 7, 2010.

(30) Foreign Application Priority Data

Sep. 6, 2010   (EP) .................................... 10009218

(51) Int. Cl.
   *C07C 205/03*   (2006.01)
   *C07C 227/00*   (2006.01)

(52) U.S. Cl.
   USPC .......................................... 562/553; 562/554

(58) Field of Classification Search
   USPC ................................................ 562/553, 554
   See application file for complete search history.

(56) References Cited

U.S. PATENT DOCUMENTS 5,073,376 A * 12/1991 Kohl et al. ................... 424/451

FOREIGN PATENT DOCUMENTS

| CN | 1167669 | | 5/2002 | |
| CN | 1349976 | * | 5/2002 | ............ C07C 227/16 |
| EP | 0434088 A1 | | 6/1991 | |
| WO | 0056701 | | 9/2000 | |
| WO | WO01/76393 | * | 10/2001 | ................ A23L 1/30 |

* cited by examiner

*Primary Examiner* — Johann R Richter
*Assistant Examiner* — Mark Luderer
(74) *Attorney, Agent, or Firm* — Hoffmann & Baron, LLP

(57) ABSTRACT

The invention relates to a process for the production of L-carnitine tartrate, wherein the L-carnitine tartrate is precipitated from a reaction mixture comprising L-carnitine and tartaric acid dissolved in ethanol, the ethanol having a water content of less than 5% (w/w).

16 Claims, 1 Drawing Sheet

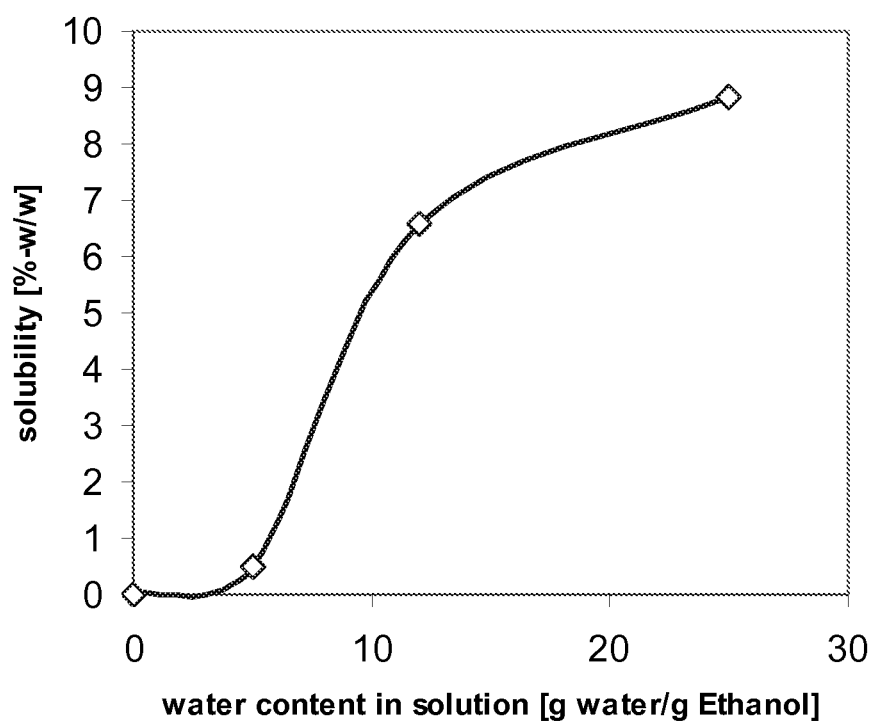

PROCESS FOR THE PRODUCTION OF L-CARNITINE TARTRATE

CROSS-REFERENCE TO RELATED APPLICATIONS

This application claims the benefit of priority from European Patent Application No. 10009218.8 filed Sep. 6, 2010 and Provisional Patent Application No. 61/380,392 filed Sep. 7, 2010, which are incorporated herein by reference.

The invention relates to methods for the production of L-carnitine tartrate.

BACKGROUND OF THE INVENTION

Carnitine (vitamin Bt; 3-hydroxy-4-trimethylammoniobutanoate) is a quaternary ammonium compound biosynthesized from the amino acids lysine and methionine. In living cells, it is required for the transport of fatty acids from the cytosol into the mitochondria during the breakdown of lipids for the generation of metabolic energy. Carnitine exists in two stereoisomers. The biologically active form is L-carnitine, whilst its enantiomer, D-carnitine, is biologically inactive.

Carnitine is widely used as a nutritional supplement in food and feed applications. However, pure carnitine is highly hygroscopic and the handling and storage is problematic. Thus for many applications it is advantageous to provide and use L-carnitine in the form of a salt.

EP 0 434 088 A1 discloses that the salt L-carnitine-L-tartrate is stable at normal air moisture during storage and can be processed without special precautions. It forms a crystalline powder, which can be easily processed and is particularly suitable for processing with rapidly running machines, since it does not tend to stick together or become lumpy. Moreover, it is odourless and has a refreshing taste due to the tartaric acid. The inventors suggest producing L-carnitine L-tartrate by adding L-carnitine crystals to a solution of L-tartaric acid in hot 90% aqueous ethanol. The method requires the use of highly pure crystalline L-carnitine, which is relatively complicated to manufacture and hygroscopic.

WO00/56701 discloses a method for preparing L-carnitine tartrate by mixing solid L-carnitine with tartaric acid in the presence of a low amount of water. The crystals are obtained after heating, cooling and grinding the mixture.

In order to improve the method of EP 0 434 088 A1, it is suggested in CN 1167669-C to obtain L-carnitine L-tartrate in a process starting from a water-containing 10% (w/v) decoloured crude L-carnitine solution. After heating the solution to a temperature between 70° C. and 78° C., a calculated dose of L-tartaric acid is added. The mixture is heated for 0.3 to 2 hours and cooled to a temperature below 10° C. After filtering, washing and drying, precipitated carnitine tartrate crystals are isolated. The inventors include a comparative example relating to EP 0 434 088 A1 and conclude that their novel process would be simpler, avoid solvents required for the production of pure L-carnitine crystals and provide higher yields.

Since L-carnitine tartrate is an important industrial product, there is an ongoing need to improve processes for its production and to render them more efficient. Since large amounts of reactants are required in such industrial processes, it is important to render such processes more efficient regarding energy consumption. Further, it is desirable to reduce the amounts of reactants and solvents and to use reactants which are easily available. CN 1167669-C requires a relatively high temperature between 70 to 78° C. as well as a relatively low temperature below 10° C., which requires cooling. Further, relatively high amounts of ethanol are necessary for the process, and the yield of L-carnitine in the best embodiment (according to the inventors) of example 3 was 89.6% in combination with an L-carnitine content of 64.6% in the crystals, which indicates that a significant amount of the starting compounds was not reacted.

PROBLEM UNDERLYING THE INVENTION

The problem underlying the invention is to provide a process for the production of L-carnitine tartrate which overcomes the above-mentioned problems. Specifically, the problem underlying the invention is to provide a process which is energy-efficient and avoids high and low temperatures. The process should require relatively low amounts of reactants and solvents and yield L-carnitine tartrate in high amounts, as well as crystals comprising a relatively high L-carnitine content. The process shall be relatively simple and the reactants shall be readily available.

DISCLOSURE OF THE INVENTION

Surprisingly, the problem underlying the invention is solved by the process according to the claims. Further inventive embodiments are disclosed throughout the description.

Subject of the invention is a process for the production of L-carnitine tartrate, wherein the L-carnitine tartrate is precipitated from a reaction mixture comprising L-carnitine and tartaric acid, the reaction mixture being dissolved in ethanol having a water content of less than 5% (w/w).

In a preferred embodiment of the invention, the process comprises the steps of
  (a) providing a solution of L-carnitine in ethanol, and
  (b) adding a solution of tartaric acid or of a tartrate in ethanol, or adding tartaric acid or a tartrate.

According to the invention, it was found that the overall process can be carried out more efficiently when the water content in the reaction mixture is relatively low. It was found that the overall reaction can then be carried out more energy-efficient and has various other advantages as outlined and shown further below. Thus it is preferred to select reagents and conditions, such that a low water content in the reaction mixture is adjusted.

Ethanol is known to comprise low amounts of water, which are difficult to remove in the industrial ethanol production and purification process. According to the invention, the term "ethanol" refers to an ethanol solvent comprising less than about 5% (w/w) water. Commercially available technical grade ethanol usually comprise between 2% and 4% (w/w) water, whereas "pure" ethanol comprises about 0.2% (w/w) water. In the inventive process, the water content in the reaction mixture is mainly a result of the water content in the ethanol used in steps (a) and (b).

Without being bound to theory, it is assumed that the strong improvements of the inventive process are associated with the low solubility of L-carnitine tartrate in ethanol comprising no water or only low amounts of water. The solubility of L-carnitine tartrate in ethanol is decreased dramatically when reducing the water content to below 5%. The relationship of L-carnitine tartrate solubility to the water content of ethanol is shown in the scheme of FIG. 1. Since L-carnitine is almost insoluble in ethanol comprising less than 5% water, the precipitation of the salt is strongly increased when mixing tartaric acid and carnitine in such a solvent. Thereby, high yields are obtained even when avoiding extreme temperatures for heating and cooling.

In preferred embodiments of the invention, the water content of the ethanol in the reaction mixture is preferably less than 4.5% (w/w) or less than 4% (w/w). More preferably, the reaction mixture comprises below 2%, below 1%, below 0.5% (w/w), below 0.2% or below 0.1% (w/w) water. In line with this, it is preferred that the ethanol in step (a) and/or the ethanol in step (b) comprises below 5% or below 4% (w/w) water, or below 2% (w/w), below 1% (w/w), below 0.5% (w/w) or below 0.1% (w/w) water.

According to the invention, it is preferred to use the inner salt of L-carnitine for preparing the L-carnitine solution in step (a). In step (b), it is preferred to add tartaric acid or a solution of tartaric acid in ethanol. Alternatively, a tartrate could be added in step (b), which is different from L-carnitine tartrate. However, when providing a tartrate into the reaction mixture, a concurring precipitation reaction could occur. When using a tartrate in step (b), it should have a solubility in ethanol, which is significantly higher than that of L-carnitine tartrate. Preferred tartrates in step (b) may be alkali metal or alkali earth metal tartrates, such as sodium or potassium tartrate.

In a preferred embodiment of the invention, the tartaric acid is L-tartaric acid and the tartrate is L-tartrate. The reaction is carried out at enhanced temperature. Thus, it is preferred to provide the solutions in steps (a) and/or step (b) at enhanced temperature. The amounts of L-carnitine and tartaric acid are adjusted such that a high yield of salt is obtained. Preferably, the amounts are selected such that the molar ratio of carnitine to tartrate is about 2:1, which is the stoichiometric ration in the salt. The molar ratio of carnitine: tartrate in the reaction mixture may also be between 2:0.8 and 2:1.2.

In a preferred embodiment of the invention, the concentration of L-carnitine in step (a) and/or the concentration of tartaric acid in step (b) and/or the concentration of L-carnitine and/or tartaric acid in the reaction mixture are 5% to 50% (w/w), base on the total weight of each solution. More preferably, the concentration of L-carnitine in the reaction mixture is between 5% and 30%, more preferably between 12% and 25% (w/w), based on the total weight of the reaction mixture. Preferably, the concentration of tartaric acid in the reaction mixture is between 3% and 20%, more preferably between 5% and 10% (w/w), based on the total weight of the reaction mixture. The concentrations in the solutions in steps (a) and (b) are adjusted such that these concentrations are obtained when mixing the carnitine and tartrate solutions. For example, a preferred concentration of the L-carnitine solution in step (a) is between 5% and 50%, more preferably between 15 and 40% (w/w), and a preferred concentration of the tartaric acid solution in step (b) is between 5% and 50%, more preferably between 10% and 30% (w/w). The concentrations and temperatures are adjusted such that the carnitine solution in step (a) and the tartrate solution in step (b) are clear solutions. When preparing the solutions, they are preferably stirred until they are clear solutions. The carnitine solution provided in step (a) may be obtained by dissolving L-carnitine in ethanol. In a preferred embodiment, the carnitine solution is a product from an industrial process for the production of carnitine. In this embodiment, the isolation of carnitine crystals and subsequent solution in ethanol is not necessary, which renders the overall process more efficient.

In a preferred embodiment of the invention, the reaction mixture is incubated at least temporarily at a temperature between 40° C. and 69° C. More preferably, the temperature is set between 50 and 69° C. Preferably, the temperature between is about 65° C. The term "at least temporarily" reflects that the reaction mixture could also be incubated temporarily at a temperature below 40° C. However, it was found not necessary for obtaining a high yield to incubate the reaction mixture at temperatures significantly above 69° C. Specifically, an incubation for extended times at a temperature between 70° C. and 78° C., as required according to CN 1167669, is not necessary. Thus in a preferred embodiment, the temperature is not raised above 70° C. However, the inventive reaction could also be carried out at a temperature of at least 69° C., for example between 40° C. and 78° C. This embodiment is less preferred, because the energy consumption is high and the reaction mixture is more difficult to handle because the temperature is close to the boiling point of ethanol.

In a preferred embodiment, the reaction is not carried out under increased pressure.

In a preferred embodiment of the invention, the solution of L-carnitine in step (a) and/or the solution of tartaric acid in step (b) are provided at a temperature between 40° C. to 69° C.

In step (b), it is preferred that a solution of tartaric acid in ethanol is used. Preferably, it is added slowly to the carnitine solution. In a preferred embodiment of the invention, the tartaric acid is added in step (b) within a time period between 10 min and 4 hours. More preferably, the solution of tartrate is added within a time period between 30 minutes and 2 hours, for example within about 1 hour. It is preferred that the addition is carried out continuously, but it can also be carried out stepwise.

When adding the tartaric acid, it is observed that white solids are precipitated. However, it was found that the solution can still be mixed easily. After or during addition of the tartaric acid, the solution thus becomes a suspension comprising suspended L-carnitine crystals.

As used herein, the term "solution" relates to clear solutions as well as solutions comprising precipitated solids (suspensions). As used herein, the term "precipitate" refers to the solid formed during the process from the solution, which comprises high amounts of or consists essentially of L-carnitine tartrate crystals. Thus "precipitated" is used synonymously with "crystallized" and the "precipitate" of carnitine tartrate is a plurality of crystals. As used herein, the term "tartaric acid" also refers to mixtures of tartaric acid and the deprotonized conjugate base, i.e. tartrate. Since tartaric acid is a weak acid, it often occurs at least partly in the form of the conjugate base. When referring to the reaction mixture, the term "tartaric acid" refers to the total amount of tartaric acid and tartrate. Similarly, the term "carnitine" also relates to conjugate forms which are at least partly deprotonized.

In the inventive process, seeding crystals of L-carnitine tartrate may be added. However, it was found that the process is highly efficient without adding seeding crystals. Thus in a preferred embodiment, no seeding crystals are added.

After combining the carnitine and tartaric acid solutions, the reaction mixture may be further incubated at enhanced temperature. During incubation, the solution is preferably stirred. In a preferred embodiment of the invention, after addition of the tartaric acid or tartaric acid solution in step (b) the process comprises a step (c) incubating the reaction mixture at a temperature between 40° C. and 69° C.

Preferably, the reaction mixture is incubated at a temperature between 50° C. and 69° C., most preferably about 65° C. It is not necessary according to the invention to incubate the reaction mixture at a temperature above 70° C. Preferably, the incubation in step (c) is carried out for example for a time period between 1 min to 2 hours, more for a time period between 10 minutes and 60 minutes, for example for about 30 minutes.

As outlined above, the inventive process is based on the finding that carnitine tartrate has a very low solubility in ethanol comprising low amounts of water. In the inventive process, the L-carnitine tartrate is precipitated at elevated temperature. Due to the very low solubility of the L-carnitine tartrate, it is not necessary to cool the reaction mixture in order to obtain high yields. However, it is suggested to cool the reaction mixture before isolation of the crystals for practical reasons, because hot crystals tend to lump together and because working with ethanol at elevated temperature is hazardous for the workers. Thus in a preferred embodiment of the invention, the process comprises after step (b) or step (c) a subsequent step of (d) reducing the temperature.

In preferred embodiments, the temperature is reduced to about 40° C. or to room temperature. It is further preferred to reduce the temperature to a temperature between 20° C. and 40° C. Preferably, the solution is stirred during step (d). Although the yield will be already high, it might be increased further during cooling. It is thus preferred that the temperature is reduced slowly for uniform additional crystal formation. The reduction of the temperature to room temperature may be carried out within a time period between 10 minutes and 5 hours, preferably between 30 minutes and 3 hours, more preferably between 1 and 2 hours. The term "room temperature" as used herein relates to a temperature between 20° C. and 30° C., or between 25° C. to 30° C. Room temperature may also specifically refer to a temperature about 20° C. or 25° C. When the temperature of the environment is above 25° C., the term "room temperature" rather relates to a temperature of about 30° C.

In a specific embodiment, the reduction of temperature is achieved by letting the reaction mixture cool down without electric cooling means or without a coolant, the temperature of which is kept below room temperature with cooling means. Such cooling means are devices or measures which consume cooling energy. According to the invention, it is not necessary to cool the reaction mixture further to a temperature below room temperature. Specifically, the reaction mixture is preferably not cooled further to a temperature below 15° C., below 10° C. or equal to or below 0° C. According to the invention, it was found that when precipitating L-carnitine tartrate from ethanol having a low water content, the yield is high when cooling the solution to room temperature only. Since the cooling of large-scale industrial processes requires high amounts of energy, the inventive process is energy-efficient. In contrast, the process of CN 1167669-C, which uses ethanol with a high water content in which L-carnitine tartrate is soluble, requires cooling to a temperature below 10° C. for obtaining a good product yield.

However, according to the invention, the cooling process may be supported by bringing the reactor in contact with a cooling liquid, such as water or oil. The cooling liquid might be used for transporting and storing the heat. The time required for cooling the reactor to room temperature may be between 30 minutes and 24 h, depending on the size of the reactor, the temperature, the surrounding conditions and cooling means, such as water.

In a preferred embodiment of the invention, the process comprises separating precipitated L-carnitine tartrate crystals from the reaction mixture and drying the crystals. The crystals may be separated by known means, for example by filtration, preferably with a Nutsch filter or by centrifugation. The crystals are dried by known means. Preferably, the crystals are washed before drying once or several times.

In a preferred embodiment of the invention, the process comprises the steps of (a) providing a 5% to 50% (w/w) solution of L-carnitine in ethanol at a temperature of 40° C. to 69° C.,
(b) adding a 5% to 50% (w/w) solution of L-tartaric acid in ethanol to obtain a reaction mixture, the ethanol in the reaction mixture having a water content of less than 5% (w/w), wherein the temperature of the reaction mixture is 40° C. to 69° C.,
(c) optionally incubating the reaction mixture further at a temperature between 40° C. to 69° C.,
(d) optionally reducing the temperature to a temperature between 20° C. and 40° C.,
(e) separating precipitated L-carnitine L-tartrate crystals from the reaction mixture and drying the crystals.

The steps are carried out in the order (a) to (e).

In a preferred embodiment of the invention, the ethanol is recycled and reused in the process. It was found that the inventive process in the presence of only low amounts of water, or neglectable amounts of water, is advantageous for recycling and reusing the solvent. For example, in the process of CN 1167669-C, wherein 95% ethanol comprising at least 5% water is used, due to the different boiling points of water and ethanol the recycling by distillation would yield a distillate having a different water content. When reusing the solvent repeatedly, it would thus not be possible to carry out the process uniformly due to variations of the composition. In contrast, when using ethanol having a low water content according to the invention, solvent variations after distillation are neglectable and the solvent can be recycled and reused repeatedly. No additional steps are necessary for removing water from the solvent during recycling.

In a specific embodiment, the ethanol is not decoloured ethanol. The use of decoloured ethanol, which is required according to CN 1167669-C, is not necessary according to the invention.

It was found that high yields of L-carnitine tartrate are obtainable according to the invention. Further, the content of the L-carnitine in the salt is relatively high. This is advantageous, because usually L-carnitine tartrate is used for supplying L-carnitine, whereas tartrate is a carrier substance. In a preferred embodiment of the invention, the yield of L-carnitine tartrate, based on the initial amount of L-carnitine, is at least 90%. More preferably, the yield of L-carnitine tartrate is at least 92% or at least 95%. Preferably, the content of L-carnitine in the crystals is at least 65%, at least 66% or at least 67% (w/w). The enantiomeric excess in the crystals depends on the enantiomeric excess of the L-carnitine used. When using pure L-carnitine, enantiomeric excesses of at least 99%, preferably more than 99.5% e/e are obtainable.

The inventive process solves the problems underlying the invention. The process is relatively simple and more efficient than conventional processes regarding energy consumption and use of reactants and solvents. The precipitation can be carried out at relatively low temperatures and cooling of the reaction mixture to temperatures below room temperature is not necessary. The yield is high and the crystals comprise high amounts of L-carnitine. Since the solvent comprises only low amounts of water, it can be recycled and reused in the process. Thus the overall consumption of raw materials and solvent is decreased. It is not necessary to provide highly pure crystalline L-carnitine.

FIG. 1

FIG. 1 shows the solubility of L-carnitine tartrate in ethanol in relation to the water content of the ethanol.

EXAMPLES

Preparation of the L-Carnitine Solution

A 500 ml laboratory reactor is charged with 123.8 g of ethanol. Then 41.2 g of carnitine is added. The reactor is closed and heated up to 65° C. until all solids have been dissolved. The stirrer is set to 500 RPM.
Preparation of the L-Tartrate Solution:
Preparation of the L-Tartrate Solution:

In a second vessel or flask, 18.77 g of L-tartaric acid are dissolved in 66.5 g of ethanol at room temperature.
Precipitation:

Within 60 min or longer the solution of the tartaric acid is fed into the carnitine solution. Mixing and reactor temperature are controlled and kept constant.
Cooling:

After complete addition of the tartaric acid the suspension is stirred for another 30 min and cooled down to 30° C. within 140 minutes or longer with a cooling liquid. At 30° C. the suspension is stirred again for 30 minutes or longer.
Product Isolation:

The solids are filtered off via a Büchner funnel and washed with 75 g of ethanol at room temperature. Then solids are dried at 60° C. and <100 mbar.

Approx. 55 g (91.7%) of dried solids are obtained. The content of D-carnitine is <=0.1% (based on total carnitine). The crystals comprise 67.2% w/w of L-carnitine.

The invention claimed is:

1. A process for the production of L-carnitine tartrate, wherein the L-carnitine tartrate is precipitated from a reaction mixture comprising L-carnitine and tartaric acid, the reaction mixture being dissolved in ethanol having a water content of less than 5% (w/w).

2. The process of claim 1, comprising the steps of
   (a) providing a solution of L-carnitine in ethanol, and
   (b) adding a solution of tartaric acid or of a tartrate in ethanol, or adding tartaric acid or a tartrate.

3. The process of claim 1, wherein the water content of the ethanol in the reaction mixture is less than 4.5% (w/w).

4. The process of claim 2, wherein the water content of the ethanol in the reaction mixture is less than 4% (w/w).

5. The process of claim 1, wherein the tartaric acid is L-tartaric acid and the tartrate is L-tartrate.

6. The process of claim 2, wherein the concentration of L-carnitine in step (a) and/or the concentration of tartaric acid in step (b) and/or the concentration of L-carnitine and/or tartaric acid in the reaction mixture are 5% to 50% (w/w).

7. The process of claim 1, wherein the reaction mixture is incubated at least temporarily at a temperature between 40° C. and 69° C.

8. The process of claim 2, wherein the solution of L-carnitine in step (a) and/or the solution of tartaric acid in step (b) are provided at a temperature between 40° C. to 69° C.

9. The process of claim 2, wherein in step (b) the tartaric acid is added within a time period between 10 min and 4 hours.

10. The process of claim 2, comprising after (b) a step of
    (c) incubating the reaction mixture at a temperature between 40° C. to 69° C. for a time period of 1 min to 2 hours.

11. The process of claim 10, comprising after step (b) or after step (c) a step
    (d) reducing the temperature to a temperature between 20° C. and 40° C.

12. The process of claim 11, comprising after step (d) a step
    (e) separating precipitated L-carnitine tartrate crystals from the reaction mixture and drying the crystals.

13. The process of claim 1, comprising the steps of
    (a) providing a 5% to 50% (w/w) solution of L-carnitine in ethanol at a temperature of 40° C. to 69° C.,
    (b) adding a 5% to 50% (w/w) solution of L-tartaric acid in ethanol to obtain a reaction mixture, wherein the ethanol in the reaction mixture has a water content of less than 5% (w/w), wherein the temperature of the reaction mixture is 40° C. to 69° C.,
    (c) optionally incubating the reaction mixture further at a temperature between 40° C. to 69° C.,
    (d) optionally reducing the temperature to a temperature between 20° C. and 40° C., and
    (e) separating precipitated L-carnitine L-tartrate crystals from the reaction mixture and drying the crystals.

14. The process of claim 1, wherein the ethanol is recycled and reused in the process.

15. The process of claim 1, wherein the yield of L-carnitine tartrate based on the initial amount of L-carnitine is at least 95%, and/or wherein the L-carnitine content in the L-carnitine tartrate is at least 65% (w/w).

16. The process of claim 2, wherein white solids are precipitated when adding the solution of tartaric acid or of the tartrate in ethanol, or when adding the tartaric acid or the tartrate.

* * * * *